US006461603B2

(12) United States Patent
Bentley et al.

(10) Patent No.: US 6,461,603 B2
(45) Date of Patent: Oct. 8, 2002

(54) WATER-SOLUBLE POLYMER CONJUGATES OF ARTELINIC ACID

(75) Inventors: Michael David Bentley, Huntsville, AL (US); Xuan Zhao, Huntsville, AL (US); Jeremy Lloyd Clark, Harvest, AL (US)

(73) Assignee: Shearwater Corporation, Huntsville, AL (US)

(*) Notice: Subject to any disclaimer, the term of this patent is extended or adjusted under 35 U.S.C. 154(b) by 0 days.

(21) Appl. No.: 09/794,731

(22) Filed: Feb. 27, 2001

(65) Prior Publication Data

US 2001/0041172 A1 Nov. 15, 2001

Related U.S. Application Data

(60) Provisional application No. 60/185,544, filed on Feb. 28, 2000.

(51) Int. Cl.[7] .................. A61K 31/80; A61K 31/74; A61K 31/335; A61K 3/35; A61K 31/34
(52) U.S. Cl. ............... 424/78.19; 424/78.31; 514/449; 514/450; 514/451; 514/468
(58) Field of Search .............. 424/78.19, 78.31; 514/449, 450, 451, 468

(56) References Cited

U.S. PATENT DOCUMENTS

| | | | |
|---|---|---|---|
| 4,791,135 A | * 12/1988 | Lin et al. | 514/450 |
| 5,648,506 A | * 7/1997 | Desai et al. | 549/510 |
| 5,677,468 A | 10/1997 | Zheng et al. | |
| 5,830,986 A | 11/1998 | Merrill et al. | |
| 5,840,900 A | 11/1998 | Greenwald et al. | |
| 5,840,925 A | 11/1998 | Zheng et al. | |
| 5,856,351 A | 1/1999 | Zheng et al. | |
| 5,874,500 A | 2/1999 | Rhee et al. | |
| 5,932,462 A | 8/1999 | Harris et al. | |
| 6,004,997 A | 12/1999 | Zheng et al. | |
| 6,156,790 A | 12/2000 | Posner et al. | |
| 6,160,004 A | 12/2000 | Posner et al. | |

FOREIGN PATENT DOCUMENTS

WO    WO 98/24786    6/1998

OTHER PUBLICATIONS

Yeh et al, "Intestinal Transport of Pegylated small Drug Molecule", 27th International Synposiumm on Release of Bioactive Materials and the Third Consumer and Diversified conference, held Jul. 7–13, 2000.*

Bentley et al., "Peg–Linked Artemisinin Antimalarials", *Polymer Preprints*, 1997, pp. 584–585, vol. 38.

Yeh, et al., "Intestinal Transport of a Pegylated Small Drug Molecule", *Proceed. Int'l. Symp. Control. Rel. Bioact. Mater.*, 2000, vol. 27, Jul. 7, 2000.

* cited by examiner

*Primary Examiner*—Thurman K. Page
*Assistant Examiner*—Blessing Fubara
(74) *Attorney, Agent, or Firm*—Alston & Bird LLP

(57) ABSTRACT

The present invention provides water-soluble polymer conjugates of the anti-malarial drug, artelinic acid, using water soluble and non-peptidic polymer backbones, such as poly (ethylene glycol). The invention includes conjugates made using mPEG, bifunctional PEG and multi-arm PEG. The invention further includes a method of forming such conjugates and a method of treating malaria using the conjugates.

38 Claims, 1 Drawing Sheet

- Effects of different doses of 4-arm 20 KDa PEG artelinate on the fraction of mice aparasitic on days 7 and 28 after treatment on day 0

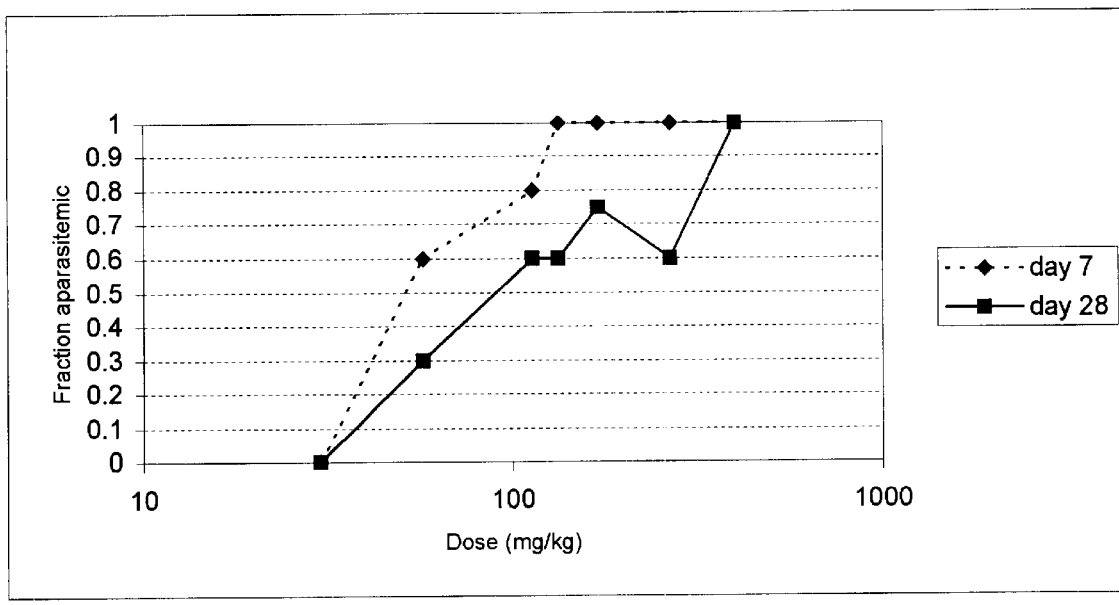
Figure 1 - Effects of different doses of 4-arm 20 KDa PEG artelinate on the fraction of mice aparasitic on days 7 and 28 after treatment on day 0

WATER-SOLUBLE POLYMER CONJUGATES OF ARTELINIC ACID

CROSS-REFERENCE TO RELATED APPLICATIONS

This application claims the benefit of U.S. Provisional Application No. 60/185,544, filed Feb. 28, 2000, which is incorporated by reference herein in its entirety.

FIELD OF THE INVENTION

This invention relates to water-soluble polymer conjugates of biologically active molecules.

BACKGROUND OF THE INVENTION

Artelinic acid, which is described in U.S. Pat. No. 4,791,135 and shown below, is a potentially useful drug for treatment of malaria. In addition, artelinic acid may prove useful as an anti-viral, anti-cancer, anti-bacterial or anti-fungal agent. One problem in using artelinic acid as a drug is its low water solubility. This can be improved by using the salt form, sodium artelinate. However, this salt is not highly soluble at physiological pH and a higher pH is required for desirable solubility levels.

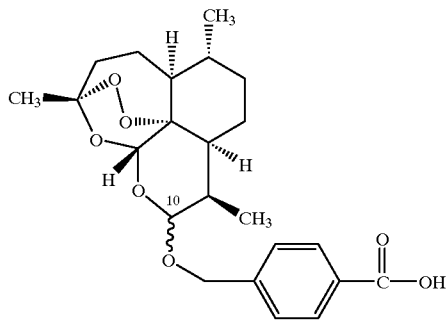

Artelinic acid

There is thus a need for derivatives of artelinic acid which are highly water-soluble at physiological pH and which can be delivered over a range of useful doses.

SUMMARY OF THE INVENTION

The present invention provides water-soluble polymer conjugates of the anti-malarial drug, artelinic acid, using water soluble and non-peptidic polymer backbones, such as poly(ethylene glycol). The conjugates having an ester linkage between the artelinic acid moiety and the polymer backbone are prodrugs, meaning that the ester linkage hydrolyzes to liberate the parent drug, artelinic acid.

The polymer conjugates of artelinic acid comprise a water soluble and non-peptidic polymer backbone, such as PEG, having at least one terminus bonded to the following structure:

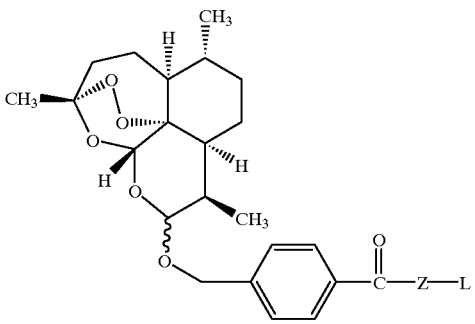

wherein L is the point of attachment to the terminus of the polymer backbone and Z is a linker, such as O or NH. Examples of the polymer backbone include poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

The polymer conjugates of the invention may comprise linear polymer backbones, such as mPEG or bifunctional PEG, or multi-arm polymer backbones. The invention includes heterobifunctional polymer conjugates wherein one terminus of the polymer backbone is attached to the artelinic acid moiety and the other terminus is functionalized with a different moiety. Additionally, the invention includes homo-bifunctional polymer conjugates, wherein both termini of the polymer backbone are bonded to artelinic acid moieties.

The invention also provides a method of forming a polymer conjugate of artelinic acid. The method includes the step of providing a water soluble and non-peptidic polymer backbone having at least one terminus bonded to a functional group reactive with a carboxylic acid group, such as hydroxyl or amine. The polymer backbone is reacted with artelinic acid to form a polymer conjugate of artelinic acid having, for example, an amide or ester linkage between the polymer backbone and the artelinic acid moiety.

The polymer conjugates of the invention can be used to treat malaria in a mammal by administering to the mammal an effective amount of the above-described polymer conjugates of artelinic acid. Examples of methods of administering the conjugate include subcutaneously, transdermally, intravenously, orally, or by inhalation. In one embodiment, the conjugate is administered in the form of a hydrogel.

BRIEF DESCRIPTION OF THE DRAWINGS

Having thus described the invention in general terms, reference will now be made to the accompanying drawing, wherein:

FIG. 1 graphically illustrates the effect of various doses of a PEG artelinate on the fraction of mice aparasitic on days 7 and 28 after treatment.

DETAILED DESCRIPTION OF THE INVENTION

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous medium in a matter of minutes, whereas certain esters, such as methyl or ethyl esters, require a strong catalyst in order to react with a nucleophilic group.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include carbonate linkages; imine linkages resulted from reaction of an amine and an aldehyde (see, e.g., Ouchi et al., *Polymer Preprints*, 38(1):582–3 (1997), which is incorporated herein by reference.); phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, e.g., at an end of a polymer such as PEG, and a carboxyl group of a peptide; and oligonucleotide linkages formed by a phosphoramidite group, e.g., at the end of a polymer, and a 5' hydroxyl group of an oligonucleotide.

The invention is directed to polymer conjugates of artelinic acid comprising a water soluble and non-peptidic polymer backbone having at least one terminus bonded to the following structure:

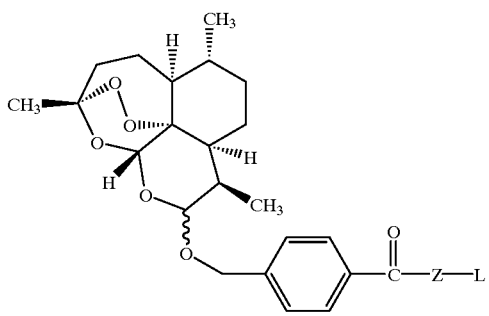

wherein L is the point of attachment to the terminus of the polymer backbone and Z is a linker.

The water-soluble and non-peptidic polymer backbone can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, bifunctional PEG, forked PEG, branched PEG, pendent PEG, or PEG with degradable linkages therein.

In its most common form, PEG is a linear polymer terminated at each end with hydroxyl groups:

$$HO-CH_2CH_2O-(CH_2CH_2O)_n-CH_2CH_2-OH$$

The above polymer, alpha-, omega-dihydroxylpoly (ethylene glycol), can be represented in brief form as HO—PEG—OH where it is understood that the —PEG— symbol represents the following structural unit:

$$-CH_2CH_2O-(CH_2CH_2O)_n-CH_2CH_2-$$

where n typically ranges from about 3 to about 4000.

PEG is commonly used as methoxy-PEG—OH, or mPEG in brief, in which one terminus is the relatively inert methoxy group, while the other terminus is a hydroxyl group that is subject to ready chemical modification. The structure of MPEG is given below.

$$CH_3O-(CH_2CH_2O)_n-CH_2CH_2-OH$$

Random or block copolymers of ethylene oxide and propylene oxide, shown below, are closely related to PEG in their chemistry, and they can be substituted for PEG in many of its applications.

$$HO-CH_2CHRO(CH_2CHRO)_nCH_2CHR-OH$$

wherein each R is independently H or $CH_3$.

An example of a forked PEG is represented by PEG(—$YCHZ_2)_n$, where Y is a linking group and Z is an activated terminal group linked to CH by a chain of atoms of defined length.

Pendant PEG has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

$$-PEG-CO_2-PEG-+H_2O \rightarrow -PEG-CO_2H+HO-PEG-$$

It is understood by those skilled in the art that the term poly(ethylene glycol) or PEG represents or includes all the above forms.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —CH$_2$CH$_2$O—(CH$_2$CH$_2$O)$_n$—CH$_2$CH$_2$—, where n is from about 3 to about 4000, typically from about 3 to about 2000, is one useful polymer in the practice of the invention. PEGs having a molecular weight of from about 200 Da to about 100,000 Da are particularly useful as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

Those of ordinary skill in the art will recognize that the foregoing list for substantially water soluble and non-peptidic polymer backbones is by no means exhaustive and is merely illustrative, and that all polymeric materials having the qualities described above are contemplated.

The Z linkage results from the reaction of a functional group on a terminus of the polymer backbone with the artelinic acid molecule. The specific linkage will depend on the type of functional group utilized. If the polymer backbone is functionalized or "activated" with a hydroxyl group, the resulting linkage will be an ester and Z will be O. If the polymer backbone is functionalized with an amine group, the resulting linkage will be an amide and Z will be NH. An ester linkage will readily hydrolyze in vivo to release artelinic acid. Other types of functional groups capable of reacting with the carboxylic acid group on the artelinic acid moiety, and consequently other types of Z linkages, could also be used within the scope of the present invention.

In one embodiment, the polymer conjugates of the invention have the following structure:

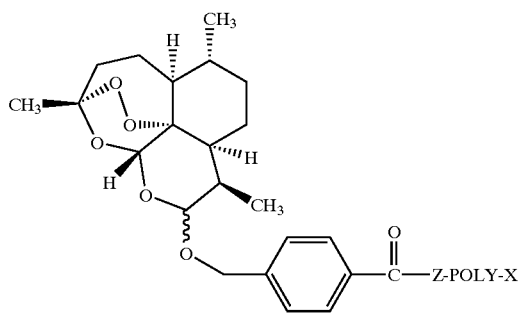

wherein POLY is a water soluble and non-peptidic polymer backbone as described above, Z is a linker as described above, and X is a capping group.

The X moiety can be any suitable capping group for polymers of the type described herein. For example, the X capping group can be a relatively inert alkoxy group (e.g. methoxy). Alternatively, the X moiety can be a functional group, such as hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, or tresylate.

As would be understood in the art, the term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention.

Specific examples of terminal functional groups in the literature include N-succinimidyl carbonate (see e.g., U.S. Pat. Nos. 5,281,698, 5,468,478), amine (see, e.g., Buckmann et al. *Makromol. Chem.* 182:1379 (1981), Zaplipsky et al. *Eur. Polym. J.* 19:1177 (1983)), hydrazide (See, e.g., Andresz et al. *Makromol. Chem.* 179:301 (1978)), succinimidyl propionate and succinimidyl butanoate (see, e.g., Olson et al. *in Poly(ethylene glycol) Chemistry & Biological Applications*, pp 170–181, Harris & Zaplipsky Eds., ACS, Washington, D.C., 1997; see also U.S. Pat. No. 5,672,662), succinimidyl succinate (See, e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g., Beauchamp, et al., *Anal. Biochem.* 131:25 (1983), Tondelli et al. *J. Controlled Release* 1:251 (1985)), p-nitrophenyl carbonate (see, e.g., Veronese, et al., *Appl. Biochem. Biotech.*, 11:141 (1985); and Sartore et al., *Appl. Biochem. Biotech.*, 27:45 (1991)), aldehyde (see, e.g., Harris et al. *J. Polym. Sci. Chem. Ed.* 22:341 (1984), U.S. Pat. No. 5,824,784, U.S. Pat. No. 5,252,714), maleimide (see, e.g., Goodson et al. *Bio/Technology* 8:343 (1990), Romani et al. *in Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules,* 26:581 (1993)), vinylsulfone (see, e.g., U.S. Pat. No. 5,900,461). All of the above references are incorporated herein by reference.

Homobifunctional polymer conjugates are also included in the present invention, wherein X has the structure:

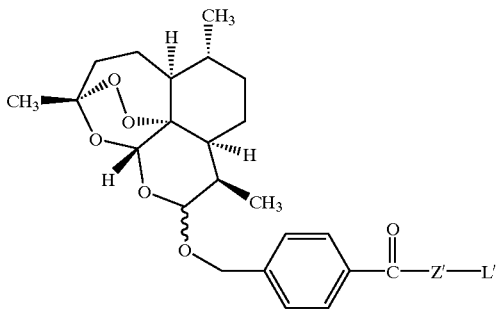

wherein Z' is a linker, such as O or NH, and L' is the point of attachment to POLY.

The invention also includes multi-arm polymer conjugates having, for example, 3 to about 100 termini. Such conjugates have the structure:

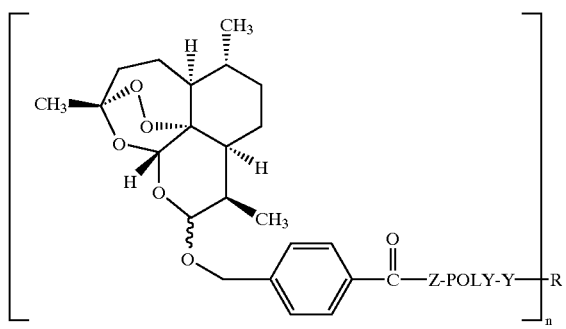

wherein:

n is an integer from 3 to about 100, preferably 3 to about 20;

R is a non-dendritic central core molecule;

Y and Z are each independently selected linkers as described above, such as O or NH; and each POLY is an independently selected water-soluble and non-peptidic polymer backbone as described above.

The central core molecule, R, is a non-dendritic molecule, meaning that the core molecule is not a dendrimer of the type described in U.S. Pat. No. 5,830,986, such as polyamidoamine dendrimers, poly(propylenimine) dendrimers and the like. Instead the R moiety is derived from a molecule selected from the group consisting of polyols, such as glycerol, glycerol oligomers, pentaerythritol or sorbitol, polyamines, such as polylysine or other polyamino acids, and molecules having a combination of alcohol and amine groups. Preferably, the molecular weight of R is less than about 2000 Da. The central core molecule is derived from a molecule having n number of functional sites capable of attaching to n number of polymer backbones, POLY, via a linkage, Y. The ability to attach a plurality of polymer backbones to the central core molecule increases the loading capacity of the polymer, which is particularly useful for biologically active agents having relatively low activity.

Specific examples of multi-arm conjugates of the invention include conjugates having the structure:

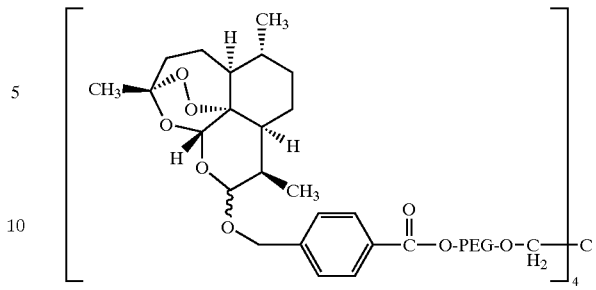

wherein PEG is poly(ethylene glycol) having an average molecular weight from about 200 Da to about 100,000 Da.

Another multi-arm conjugate of the invention has the structure:

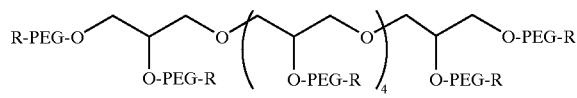

wherein PEG is poly(ethylene glycol) having an average molecular weight from about 200 Da to about 100,000 Da and R is

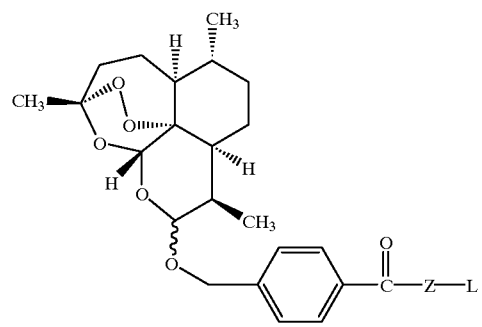

wherein Z is a linker as described above and L is the point of attachment to PEG.

The invention includes a method of forming the polymer conjugates of artelinic acid. The method includes reacting a water soluble and non-peptidic polymer backbone with artelinic acid, wherein the polymer backbone has at least one terminus bonded to a functional group selected from the group consisting of hydroxyl and amine. The hydroxyl or amine group will react with the carboxylic acid group on the artelinic acid molecule to form an amide or ester linkage between the polymer backbone and the artelinic acid moiety. As would be understood, other functional groups reactive with a carboxylic acid group could be utilized without departing from the invention. If an ester linkage is formed, the linkage will hydrolyze in vivo to release artelinic acid.

The reaction is preferably conducted in the presence of 1-hydroxybenzotriazole (HOBT), N,N-dicyclohexylcarbodiimide (DCC), and a catalytic amount of N,N-dimethylaminopyridine (DMAP). The final product may then be purified and collected by precipitation followed by filtration and drying.

The polymer conjugates of the invention can be used to treat malaria in mammals, including humans. The method of treatment comprises administering to the mammal an effective amount of a polymer conjugate of artelinic acid described above. The therapeutically effective dosage amount of any specific conjugate will vary somewhat from conjugate to conjugate, patient to patient, and will depend upon factors such as the condition of the patient, the loading capacity of the polymer conjugate, and the route of delivery. Typical routes of delivery include subcutaneously, transdermally, intravenously, orally, and inhalation. In one embodiment, the polymer conjugate is administered in the form of a hydrogel. For example, such a hydrogel may be formed by cross-linking two multi-functional polymer backbones, such as a multi-arm PEG with a bifunctional PEG.

The following examples are given to illustrate the invention, but should not be considered in limitation of the invention:

EXAMPLE 1

Preparation of mPEG$_{350}$Artelinate

Reaction:

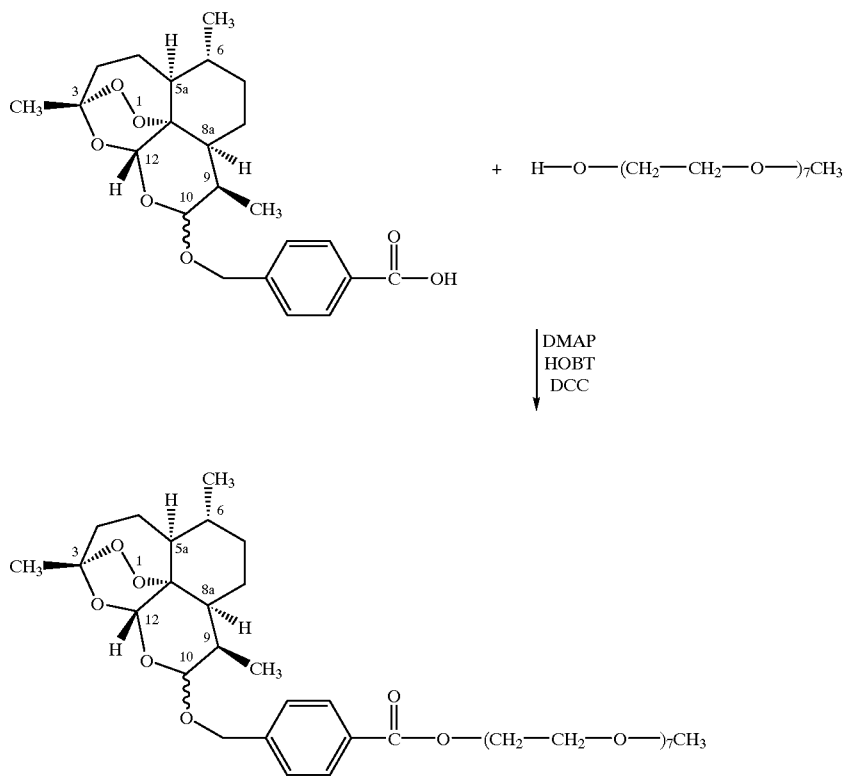

mPEG (MW 350 Da, 300 mg, 0.86 mmol) (Shearwater Corporation) was azeotropically dried in vacuo with CHCl$_3$ (2×100 ml) and was redissolved in CH$_2$Cl$_2$ (20 ml). To this clear solution was added artelinic acid (360 mg, 0.86 mmol), N,N-dimethylaminopyridine (DMAP) (catalytic amount), and 1-hydroxybenzotriazole (HOBT) (185 mg, 1.37 mmol). N,N-dicyclohexylcarbodiimide (DCC) (290 mg, 1.41 mmol in about 2 ml of CH$_2$Cl$_2$) was then added and the mixture was allowed to reflux under of argon for 17 hours. The solvent was removed by evaporation and the residue chromatographed on silica gel eluted with ethyl acetate/chloroform to yield the product as a water-soluble oil. $^1$H NMR. Partial $^1$H NMR data (CDCl$_3$, 300 MHz): δ 0.94 (s, 3H, C9—CH$_3$), 0.95 (s, 3H, C6—CH$_3$), 1.44 (s, 3H, C3—CH$_3$), 2.68 (m, 1H, H-9), 3.63 (bs, 28H, PEG backbone), 4.45 (t, 2H, J 4.4 Hz, PEG—OCH$_2$CH$_2$O—COAr), 4.56 (d, 2H, J 13.1 Hz, OCH$_A$H$_B$—Ar), 4.91–4.96 (m, 2H, H-10 overlapped with OCH$_A$H$_B$—Ar), 5.44 (s, 1H, H-12), 7.37 (d, 2H, J 7.8 Hz, Ar), 8.01 (d, 2H, Ar).

EXAMPLE 2

Preparation of PEG3400 Diartelinamide

Reaction:

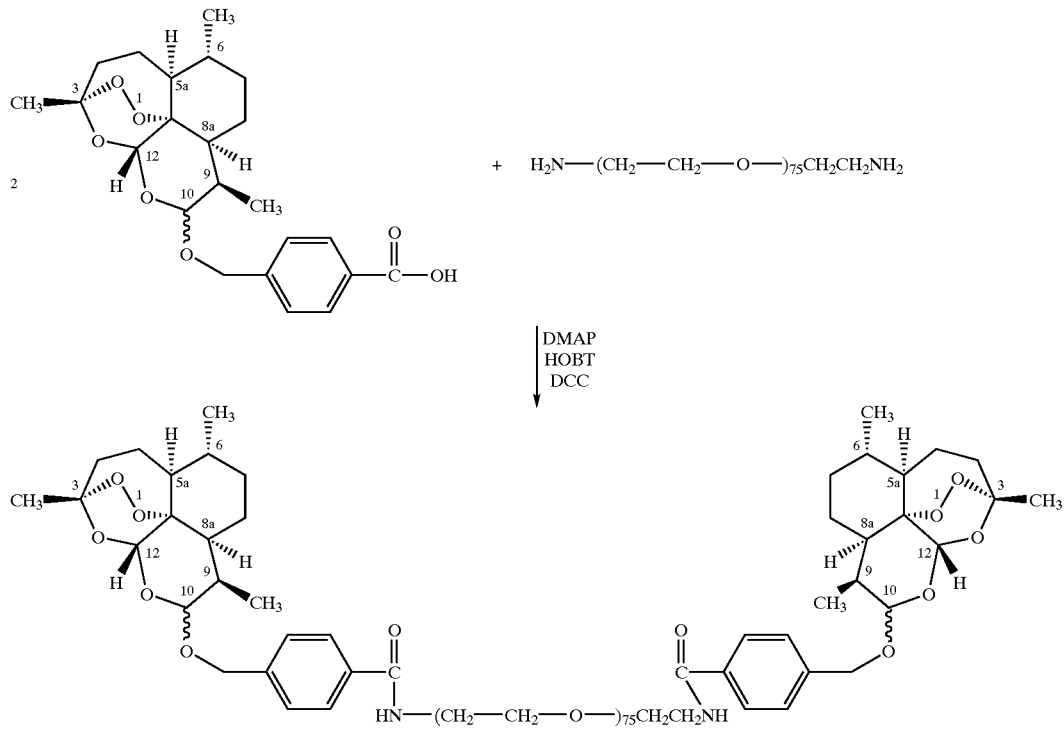

PEG diamine (MW 3400 Da, 2.0 g, 0.59 mmol) (Shearwater Corporation) was azeotropically dried in vacuo with $CHCl_3$ (3×200 ml) and was redissolved in $CH_2Cl_2$ (250 ml). To this clear solution was added artelinic acid (1.25 g, 3 mmol), N,N-dimethylaminopyridine (DMAP) (catalytic amount), and 1-hydroxybenzotriazole (HOBT) (0.24 g, 1.8 mmol). N,N-dicyclohexylcarbodiimide (DCC) (1.3 g, 6.3 mmol in about 10 ml of $CH_2Cl_2$) was then added and the mixture was allowed to reflux under argon for 17 hours. The mixture was then concentrated in vacuo and the residual syrup was dissolved in toluene (~200 ml) and filtered. The toluene was removed in vacuo at about 45° C. and the residue was treated with 5 ml of $CH_2Cl_2$ and triturated with 2-propanol (300 ml). The resulting precipitate was collected by vacuum filtration and dried in vacuo to obtain a pure water-soluble product (2 g, 81% yield) with >95% substitution as indicated by $^1H$ NMR. Partial $^1H$ NMR data $(CDCl_3$, 300 MHz): δ 0.94 (s, 6H, C9—$CH_3$), 0.95 (s, 6H, C6—$CH_3$), 1.44 (s, 6H, C3—$CH_3$), 2.68 (m, 2H, H-9), 3.63 (bs, 309H, PEG backbone), 4.56 (d, 2H, J 13.1 Hz, $OCH_AH_B$—Ar), 4.91–4.96 (m, 4H, H-10 overlapped with $OCH_AH_B$—Ar), 5.44 (s, 2H, H-12), 7.37 (d, 4H, J 7.8 Hz, Ar), 8.01 (d, 4H, Ar).

EXAMPLE 3

Preparation of 4 Arm PEG (20 KDa) Artelinate

Reaction:

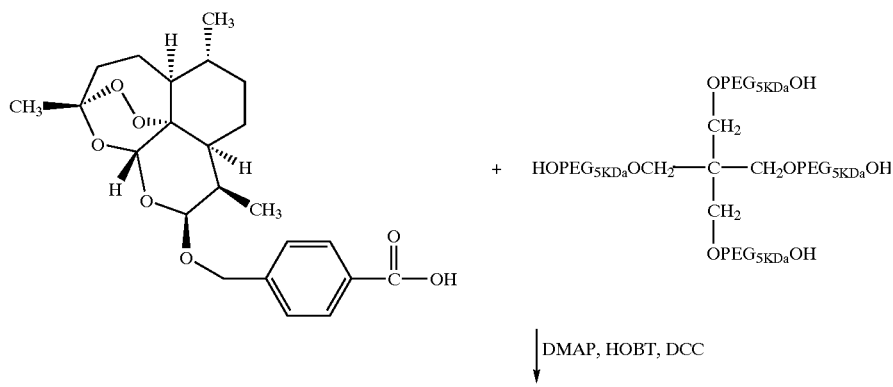

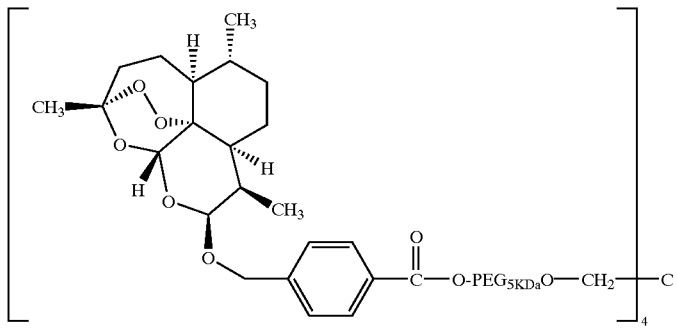

4-Arm PEG (MW 20 Kda, 20 g, ~1 mmol) (Shearwater Corporation) was azeotropically dried in vacuo with $CHCl_3$ (3×200 ml) and was redissolved in $CH_2Cl_2$ (250 ml). To this clear solution was added artelinic acid (3.30 g, 7.88 mmol), N,N-dimethylaminopyridine (DMAP) (catalytic amount), and 1-hydroxybenzotriazole (HOBT) (0.680 g, 5.03 mmol). N,N-dicyclohexylcarbodiimide (DCC) (1.74 g, 8.43 mmol in about 10 ml of $CH_2Cl_2$) was then added and the mixture was allowed to reflux under of argon for 17 hours. The mixture was then concentrated in vacuo and the residual syrup was dissolved in toluene (~200 ml) and filtered. The toluene was removed in vacuo at about 45° C. and the residue was treated with 5 ml of $CH_2Cl_2$ and triturated with 2-propanol (300 ml). The resulting precipitate was collected by vacuum filtration and dried in vacuo to obtain a pure water-soluble product (18.5 g, 92% yield) with >95% substitution as indicated by $^1H$ NMR. Partial $^1H$ NMR data ($CDCl_3$, 300 MHz): δ 0.94 (s, 12H, C9—$CH_3$), 0.95 (s, 12H, C6—$CH_3$), 1.44 (s, 12H, C3—$CH_3$), 2.68 (m, 4H, H-9), 3.63 (bs, 1818H, PEG backbone), 4.45 (t, 8H, J 4.4 Hz, PEG—$OCH_2CH_2O$—COAr), 4.56 (d, 4H, J 13.1 Hz, $OCH_AH_B$—Ar), 4.91–4.96 (m, 8H, H-10 overlapped with $OCH_AH_B$—Ar), 5.44 (s, 4H, H-12), 7.37 (d, 4H, J 7.8 Hz, Ar), 8.01 (d, 4H, Ar).

EXAMPLE 4

Preparation of 8 Arm PEG (20 KDa) Artelinamide

Reaction:

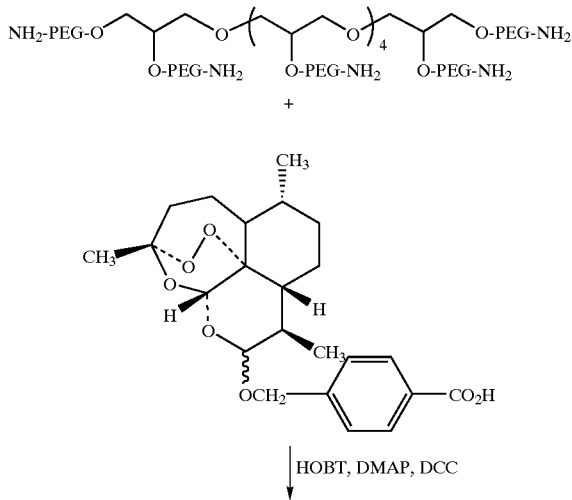

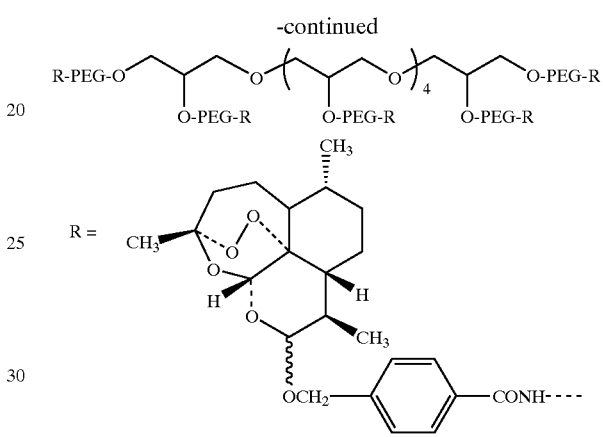

8 Arm PEG (20 KDa) amine (Shearwater Corporation) (2.5 g, ~0.13 mmol) was dissolved in $CHCl_3$ (300 mL) and the solvent was removed in vacuo. The gum was dissolved in $CH_2Cl_2$ (~30 ml) under an argon atmosphere. To the solution was then added artelinic acid (0.85 g, 2.00 mmol), 1-hydroxybenzotriazole (0.085 g, 0.63 mmol) and 4-(dimethylamino)pyridine (catalytic)). The mixture was warmed while DCC (0.60 g, 2.9 mmol in ~5 mL $CH_2Cl_2$) was added. The mixture was allowed to reflux for 2 h. Observation of $^1H$ NMR at 2.9 ppm was used to monitor the disappearance of the starting amine The cloudy mixture was concentrated to dryness and to the residue was added $CH_2Cl_2$ (~5 ml). To the slightly turbid solution was added EtOH (~100 ml) and a white solid was obtained upon cooling in an ice bath for ~3 h. Repeating the purification afforded pure 8 arm PEG (20 KDa) artelinamide (2.05 g) as a water-soluble white solid. $^1H$ NMR ($CDCl_3$, 300 MHz) indicated a near quantitative conversion. HPLC (C-4 reversed-phase) indicated a mixture of products arising from different degrees of substitution. Partial $^1H$ NMR data ($CDCl_3$, 300 MHz): δ 0.94 (s, 24H, C9—$CH_3$), 0.95 (s, 24H, C6—$CH_3$), 1.45 (s, 24H, C3—$CH_3$), 2.68 (m, 8H, H-9), 3.64 (bs, 1818H, PEG backbone), 4.56 (d, 8H, J 12.9 Hz, $OCH_AH_B$—Ar), 4.91–4.96 (m, 16H, H-10 overlapped with $OCH_AH_B$—Ar), 5.45 (s, 8H, H-12), 6.87 (apparent s, 8H, ArCONH), 7.37 (d, 16H, J 7.8 Hz, Ar), 7.79 (d, 16H, Ar).

EXAMPLE 5

8 Arm PEG (20 KDa) Artelinate

Reaction:

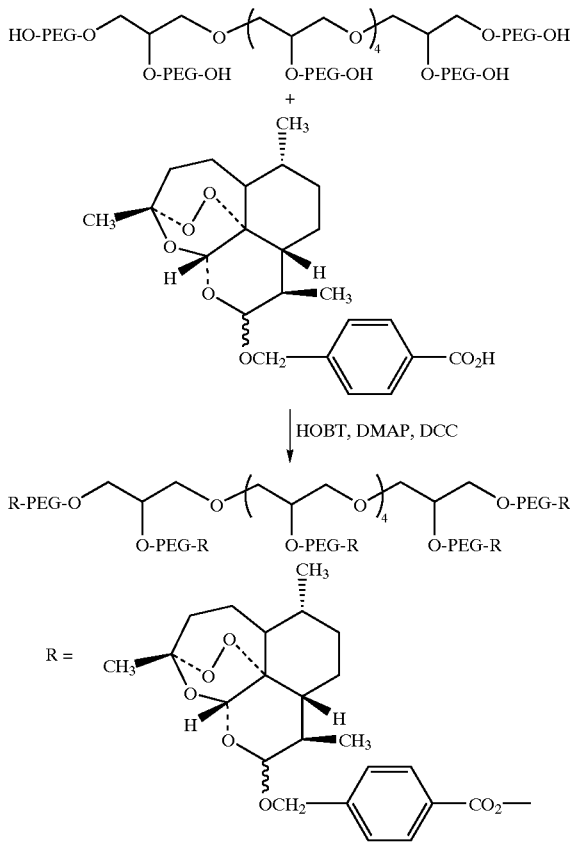

8 arm PEG (20 Kda) (2.0 g, ~0.10 mmol) was dissolved in CHCl$_3$ (300 ml) and the solvent was removed in vacuo. The gum was dissolved in CH$_2$Cl$_2$ (~30 ml) under an argon atmosphere and to the solution was added artelinic acid (0.85 g, 2.00 mmol), 1-hydroxybenzotriazole (0.085 g, 0.63 mmol) and 4-(dimethylamino)pyridine (cat.). The mixture was allowed to reflux overnight under an argon atmosphere. The cloudy mixture was concentrated to dryness and to the residue was added CH$_2$Cl$_2$ (~5 ml). To the slightly turbid solution was added EtOH (~100 ml) and a white solid was obtained upon cooling in an ice bath for ~3 h. Repeating the purification afforded pure 8 arm PEG (20 Kda) artelinate (1.00 g) as a water-soluble white solid. $^1$H NMR (CDCl$_3$, 300 MHz) indicated a near quantitative conversion. HPLC (C-4 reversed-phase) indicated a mixture of products arising from different degrees of substitution. Partial $^1$H NMR data (CDCl$_3$, 300 MHz): δ 0.94 (s, 24H, C9—CH$_3$), 0.95 (s, 24H, C6—CH$_3$), 1.44 (s, 24H, C3—CH$_3$), 2.68 (m, 8H, H-9), 3.63 (bs, 1818H, PEG backbone), 4.45 (t, 16H, J 4.4 Hz, PEG—OCH$_2$CH$_2$O—COAr), 4.56 (d, 8H, J 13.1 Hz, OCH$_A$H$_B$—Ar), 4.91–4.96 (m, 16H, H-10 overlapped with OCH$_A$H$_B$—Ar), 5.44 (s, 7.5H, H-12), 7.37 (d, 8H, J 7.8 Hz, Ar), 8.01 (d, 8H, Ar).

EXAMPLE 6

Anti-malarial Assays in Mice

Two experiments were performed with *Plasmodium berghei* (NK65)-infected mice. Each treatment dose regimen was given to at least 5 infected mice. Mice were inoculated with one million parasites intraperitoneally. PEG derivatives were prepared as artelinate esters on 4-arm PEG of molecular weight 20 KDa. This material was incorporated into a biodegradable PEG hydrogel prepared by cross-linking 8-arm 10 KDa PEG amine with a di-N-hydroxysuccinimidyl ester of a 3400 Da PEG dicarboxylic acid having two hydrolyzable esters in the PEG backbone. The hydrogels containing the PEG drugs were given subcutaneously either one day before (day −1), one hour before (day 0), or 24 hours later (day +1). The results of the experiments are shown in FIG. 1. Control mice were always parasitemic by day 7 and died between days 21 and 28. In order to make our results comparable to other studies and since there are a variety of ways that drugs are tested for anti-malarial activity in mice, we chose two endpoints. First, we report the fraction of mice that are aparasitemic on day 7. This measures a suppressive effect. The fraction of mice that are aparasitemic on day 28 is also presented. Aparasitic mice were assumed to be cured.

What is claimed is:

1. A polymer conjugate of artelinic acid comprising a water soluble and non-peptidic polymer backbone having at least one terminus bonded to the following structure:

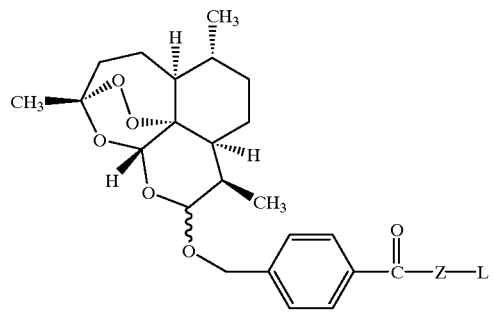

wherein L is the point of attachment to the terminus of the polymer backbone and Z is a linker.

2. The polymer conjugate of claim 1, wherein the polymer backbone is selected from the group consisting of poly (alkylene glycol), poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, poly (N-acryloylmorpholine), and copolymers, terpolymers, and mixtures thereof.

3. The polymer conjugate of claim 1, wherein the polymer backbone is poly(ethylene glycol).

4. The polymer conjugate of claim 3, wherein the poly (ethylene glycol) has an average molecular weight from about 200 Da to about 100,000 Da.

5. The polymer conjugate of claim 1, wherein Z is O or NH.

6. The polymer conjugate of claim 1, wherein the polymer backbone has about 2 to about 300 termini.

7. The polymer conjugate of claim 1, having the following structure:

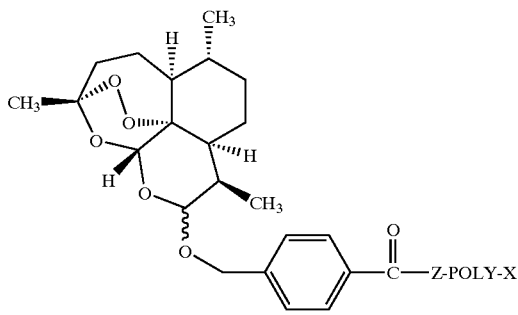

wherein POLY is a water soluble and non-peptidic polymer backbone, Z is a linker, and X is a capping group.

8. The polymer conjugate of claim 7, wherein POLY is selected from the group consisting of poly(alkylene glycol), poly(oxyethylated polyol), poly(olefinic alcohol), poly (vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

9. The polymer conjugate of claim 7, wherein POLY is poly(ethylene glycol).

10. The polymer conjugate of claim 9, wherein the poly(ethylene glycol) has an average molecular weight from about 200 Da to about 100,000 Da.

11. The polymer conjugate of claim 7, wherein Z is O or NH.

12. The polymer conjugate of claim 7, wherein X is selected from the group consisting of alkoxy, hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate.

13. The polymer conjugate of claim 7, wherein X has the structure:

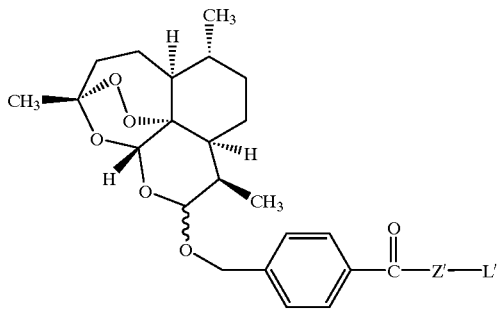

wherein Z' is a linker and L' is the point of attachment to POLY.

14. The polymer conjugate of claim 13, wherein Z' is O or NH.

15. The polymer conjugate of claim 1, having the structure:

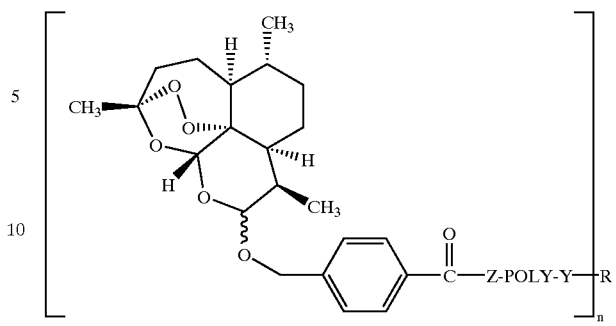

wherein:

n is an integer from 3 to about 100;

R is non-dendritic central core molecule;

Y and Z are each independently selected linkers; and each POLY is an independently selected water-soluble and non-peptidic polymer backbone.

16. The polymer conjugate of claim 15, wherein n is about 3 to about 20.

17. The polymer conjugate of claim 15, wherein each Y and Z are independently selected from the group consisting of O and NH.

18. The polymer conjugate of claim 15, wherein R is derived from a molecule selected from the group consisting of polyols, polyamines, and molecules having a combination of alcohol and amine groups.

19. The polymer conjugate of claim 15, wherein R is derived from a molecule selected from the group consisting of glycerol, glycerol oligomers, pentaerythritol, sorbitol, and lysine.

20. The polymer conjugate of claim 15, wherein POLY is selected from the group consisting of poly(alkylene glycol), poly(oxyethylated polyol), poly(olefinic alcohol), poly (vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

21. The polymer conjugate of claim 15, wherein POLY is poly(ethylene glycol).

22. The polymer conjugate of claim 21, wherein the poly(ethylene glycol) has an average molecular weight from about 200 Da to about 100,000 Da.

23. The polymer conjugate of claim 15, having the structure:

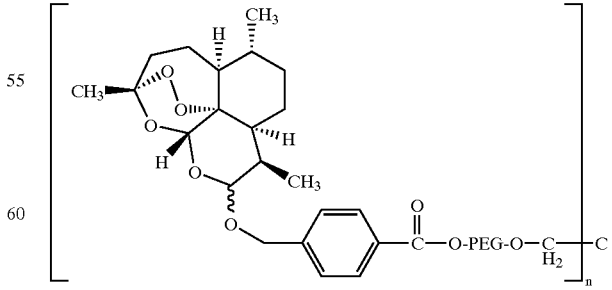

wherein PEG is poly(ethylene glycol) having an average molecular weight from about 200 Da to about 100,000 Da.

24. The polymer conjugate of claim 15, having the structure:

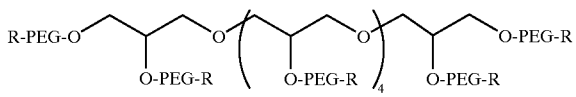

wherein PEG is poly(ethylene glycol) having an average molecular weight from about 200 Da to about 100,000 Da and R is

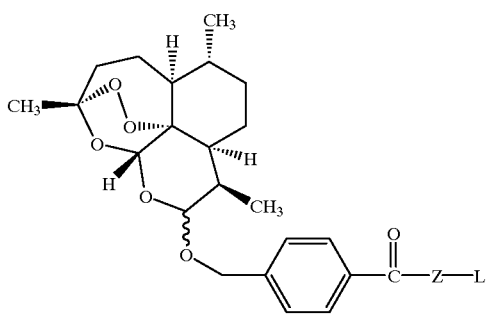

wherein Z is a linker and L is the point of attachment to PEG.

25. A method of forming a polymer conjugate of artelinic acid, comprising:
providing a water soluble and non-peptidic polymer backbone having at least one terminus bonded to a functional group reactive with a carboxylic acid group; and
reacting the polymer backbone with artelinic acid to form a polymer conjugate of artelinic acid.

26. The method of claim 25, wherein the functional group is selected from the group consisting of hydroxyl and amine.

27. The method of claim 25, wherein said reacting step comprises reacting the polymer backbone with artelinic acid in the presence of a catalytic amount of N,N-dimethylaminopyridine.

28. The method of claim 25, wherein the polymer backbone is selected from the group consisting of poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

29. The method of claim 25, wherein the polymer backbone is poly(ethylene glycol).

30. The method of claim 29, wherein the poly(ethylene glycol) has an average molecular weight from about 200 Da to about 100,000 Da.

31. A method of treating malaria in a mammal, the method comprising administering to the mammal an effective amount of a polymer conjugate of artelinic acid comprising a water soluble and non-peptidic polymer backbone having at least one terminus bonded to the following structure:

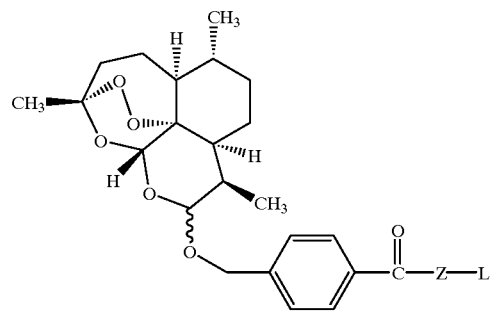

wherein L is the point of attachment to the terminus of the polymer backbone and Z is a linker.

32. The method of claim 31, wherein the polymer backbone is selected from the group consisting of poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

33. The method of claim 31, wherein the polymer backbone is poly(ethylene glycol).

34. The method of claim 33, wherein the poly(ethylene glycol) has an average molecular weight from about 200 Da to about 100,000 Da.

35. The method of claim 31, wherein Z is O or NH.

36. The method of claim 31, wherein the polymer backbone has about 2 to about 300 termini.

37. The method of claim 31, wherein said administering step comprises administering the compound subcutaneously, transdermally, intravenously, orally, or by inhalation.

38. The method of claim 31, wherein said administering step comprises administering the compound in the form of a hydrogel.

* * * * *

UNITED STATES PATENT AND TRADEMARK OFFICE
CERTIFICATE OF CORRECTION

PATENT NO. : 6,461,603 B2
DATED : October 8, 2002
INVENTOR(S) : Bentley et al.

It is certified that error appears in the above-identified patent and that said Letters Patent is hereby corrected as shown below:

Title page,
Item [56], References Cited, OTHER PUBLICATIONS,
"Synposiumm" should read -- Symposium --.

Column 18,
Lines 51-54, the structure should appear as follows:

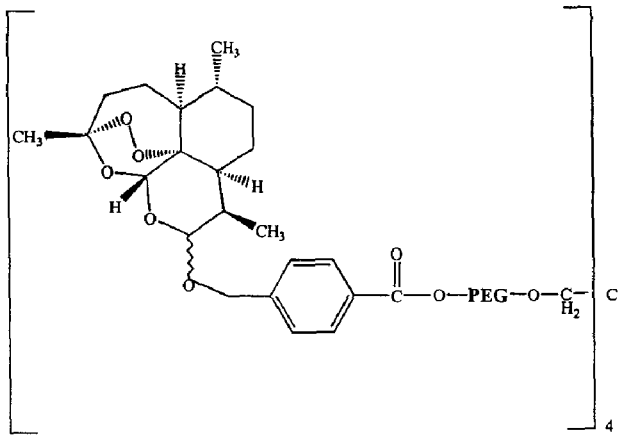

Signed and Sealed this

Twenty-fifth Day of February, 2003

JAMES E. ROGAN
*Director of the United States Patent and Trademark Office*